(12) United States Patent
Benjamin et al.

(10) Patent No.: US 11,554,188 B2
(45) Date of Patent: Jan. 17, 2023

(54) ANTI-VIRAL DRY CLEANING PROCESS

(71) Applicant: GreenEarth Cleaning, LLC, Kansas City, MO (US)

(72) Inventors: Ronald L. Benjamin, Kansas City, MO (US); Andrew T. Lien, Kansas City, MO (US); Timothy R. Maxwell, Kansas City, MO (US)

(73) Assignee: GREENEARTH CLEANING, LLC, Kansas City, MO (US)

( * ) Notice: Subject to any disclaimer, the term of this patent is extended or adjusted under 35 U.S.C. 154(b) by 0 days.

(21) Appl. No.: 17/245,578

(22) Filed: Apr. 30, 2021

(65) Prior Publication Data

US 2021/0346535 A1 Nov. 11, 2021

Related U.S. Application Data

(60) Provisional application No. 63/171,362, filed on Apr. 6, 2021, provisional application No. 63/021,788, filed on May 8, 2020.

(51) Int. Cl.
*A61L 2/07* (2006.01)
*D06F 43/00* (2006.01)
*D06L 1/20* (2006.01)

(52) U.S. Cl.
CPC ............. *A61L 2/07* (2013.01); *D06F 43/007* (2013.01); *D06L 1/20* (2013.01); *A61L 2202/17* (2013.01); *A61L 2202/26* (2013.01)

(58) Field of Classification Search
CPC .... A61L 2/07; A61L 2202/17; A61L 2202/26; D06F 43/007; D06L 1/20
See application file for complete search history.

(56) References Cited

U.S. PATENT DOCUMENTS

| | | | | |
|---|---|---|---|---|
| 4,443,344 A | * | 4/1984 | Lewis | B01D 41/04 210/791 |
| 4,520,577 A | * | 6/1985 | Suissa | D06F 43/086 62/238.7 |
| 4,781,041 A | * | 11/1988 | Fowler | A61L 2/18 68/18 F |
| 4,797,128 A | | 1/1989 | Fowler | |
| 5,653,770 A | * | 8/1997 | Goldstein | D06P 1/922 8/618 |
| 5,865,851 A | * | 2/1999 | Sidoti | D06L 1/02 510/293 |
| 6,042,618 A | | 3/2000 | Berndt | |
| 6,063,135 A | * | 5/2000 | Berndt | C11D 1/82 134/19 |
| 2003/0079298 A1 | * | 5/2003 | Runyon | D06L 1/02 68/18 F |
| 2003/0135934 A1 | * | 7/2003 | Banerjee | C11D 11/007 68/18 F |
| 2004/0088795 A1 | * | 5/2004 | Orchowski | D06L 1/02 8/142 |
| 2004/0226105 A1 | * | 11/2004 | Hayday | C11D 3/2068 8/142 |
| 2006/0059632 A1 | * | 3/2006 | Fyvie | D06F 43/086 8/158 |
| 2006/0200915 A1 | * | 9/2006 | France | D06L 1/08 8/142 |
| 2013/0345105 A1 | * | 12/2013 | Carlson | C11D 3/02 510/103 |

FOREIGN PATENT DOCUMENTS

CN 1699672 A * 11/2005 ............ D06F 35/00

OTHER PUBLICATIONS

Amy Price, et al. (2020) "Addressing COVID-19 Face Mask Shortages [v1.1]," Standford Medicine, Anesthesia Infomatics and Media Lab, Mar. 22, 2020, 1-9.
International Search Report and Written Option corresponding to International Patent Application No. PCT/US2021/030237, dated Aug. 27, 2021.

\* cited by examiner

*Primary Examiner* — Regina M Yoo
(74) *Attorney, Agent, or Firm* — Lathrop GPM LLP; Brian C. Trinque (57) ABSTRACT

Provided herein is a method of treating material that is contaminated with a virus, comprising exposing the material to vapor, wherein the vapor is produced by heating and/or vaporizing a dry cleaning solvent, and wherein the method at least partially deactivates the virus.

12 Claims, 2 Drawing Sheets

Figure 1. Coupon Heat and Vapor Test System Diagram

Figure 2. Test Results for Individual and Complete Cycle Dry Cleaning Processes

ANTI-VIRAL DRY CLEANING PROCESS

RELATED APPLICATION

This application claims priority to U.S. Provisional Application No. 63/171,362, filed Apr. 6, 2021, and U.S. Provisional Application No. 63/021,788, filed May 8, 2020. The entire contents of these application are incorporated herein by reference.

BACKGROUND

A virus is a submicroscopic infectious agent that replicates only inside the living cells of an organism. Many viruses evade immune responses from animals and humans, resulting in chronic infections. SARS-CoV-2, the virus that causes COVID-19, is not the same as the coronaviruses that commonly circulate among humans and cause mild illness, like the common cold. Although it is still unclear how long SARS-CoV-2 can survive on clothing, experts recommend caution when laundering clothes and other materials in order to help control the spread of the virus.

There remains a need to properly treat clothes, household fabric goods, and personal protective equipment to safely remove viruses.

SUMMARY OF THE INVENTION

Provided herein is a method of treating material that is contaminated with SARS-CoV-2 virus or a variant thereof, comprising exposing the material to vapor, heat, and dry cleaning solvent, wherein the vapor is produced by heating and/or vaporizing a dry cleaning solvent, and wherein the method at least partially deactivates the virus.

In an embodiment of the method, the material is exposed to the heat, vapor, and dry cleaning solvent during the washing cycle of a dry cleaning process, the drying cycle of a dry cleaning process, or a combination of both. In another embodiment of the method, the material and dry cleaning solvent are added to the chamber of a dry cleaning machine.

In an embodiment of the method, the vapor is produced during the process of vaporization, wherein a liquid is converted to a gas. In an embodiment of the method, the process of vaporization occurs, wherein the application of heat converts liquid to a gas. In another embodiment of the method, the process of vaporization occurs, wherein the application of pressure converts liquid to a gas.

In an embodiment of the method, the vapor is produced as part of a dry cleaning process. The vapor can be produced during the drying cycle of the dry cleaning process, or the washing cycle of the dry cleaning process. In an embodiment of the method, the vapor reaches a temperature of at least 70° C. In another embodiment of the method, the chamber of the dry cleaning machine is heated to a temperature of 70° C. to 85° C.

In yet another embodiment of the method, the method comprises the steps of a) exposing the material to dry cleaning solvent, followed by b) heating the dry cleaning solvent to form a vapor.

In an embodiment of the method, the dry cleaning solvent further comprises water, and vapor is produced by heating dry cleaning solvent and water.

In an embodiment of the method, the material is exposed to the vapor for 3-75 minutes.

In an embodiment of the method, the material is a fabric. In a further embodiment, the fabric is an article of clothing or household fabric item. In yet another embodiment, the material comprises polypropylene fibers.

In an embodiment of the method, the vapor is produced as part of a dry cleaning process. In a further embodiment, the vapor is produced during the drying cycle of a dry cleaning process. In yet another embodiment, the vapor is produced during the washing cycle of a dry cleaning process. In an embodiment, the vapor reaches a temperature of at least 70° C. In another embodiment of the method, the chamber of the dry cleaning machine is heated to a temperature of 70° C. to 85° C.

In an embodiment, the dry cleaning solvent has a flash point of at least 60° C. In an embodiment, the material is exposed to the vapor for 3-75 minutes. In an embodiment, the vapor is produced by heating and/or vaporizing a dry cleaning solvent and water.

In an embodiment, the virus has a lipid-containing coating, and the method destroys the lipid-containing coating. In an embodiment, the vapor comprises submicron liquid particles of solvent that penetrate the lipid coating of the virus. In an embodiment, the virus has a lipid-containing coating or envelope, and the method destroys or disrupts the lipid-containing coating.

In an embodiment, the vapor comprises submicron liquid particles of solvent that penetrate the lipid-containing coating of the virus.

In an embodiment of the method, the vapor is produced by heating and/or vaporizing a dry cleaning solvent and water. In a further embodiment, the vapor comprises submicron liquid particles of solvent that penetrate the lipid-containing coating of the virus.

In an embodiment of the method, the dry cleaning solvent is a siloxane-based solvent. In a further embodiment of the method, the siloxane-based solvent is decamethylcyclopentasiloxane (D5), octamethyltetracyclosiloxane, or dodecamethylhexacyclosiloxane. In still another embodiment of the method, the siloxane-based solvent is decamethylcyclopentasiloxane (D5).

In another embodiment of the method, the vapor is produced in a rotating drum, where said drum tumbles the material such that the material is contacted by the vapor. In still another embodiment of the method, the vapor is injected into the rotating drum at a pressure of 0.5 psi-1000 psi.

In yet another embodiment of the method, the fabric is an article of clothing or a fabric household good. In another embodiment of the method, the material comprises wool, polyester and/or polyester blend fibers. In yet another embodiment of the method, the material comprises cotton, hemp, wool, rayon, polyester, acrylic, silk, or nylon, or blends thereof.

In another aspect, provided herein is a method of treating material that is contaminated with SARS-CoV-2 virus or a variant thereof, comprising exposing the material to a dry cleaning solvent, followed by a drying step at 45° C.-85° C. wherein the solvent is removed, wherein the method at least partially deactivates the virus.

In an embodiment, the method is part of a dry cleaning process.

In an embodiment of the method, the drying cycle takes place over 3-75 minutes.

In an embodiment of the method, the dry cleaning solvent is a siloxane-based solvent. In a further embodiment, the siloxane-based solvent is decamethylcyclopentasiloxane (D5), octamethyltetracyclosiloxane, or dodecamethylhexacyclosiloxane. In a preferred embodiment, the siloxane-based solvent is decamethylcyclopentasiloxane (D5).

In another embodiment of the method, the material is a fabric. In another embodiment of the method, the fabric is an article of clothing or a fabric household good. In another embodiment of the method, the material comprises wool, polyester and/or polyester blend fibers. In yet another embodiment of the method, the material comprises cotton, hemp, wool, rayon, polyester, acrylic, silk, or nylon, or blends thereof. In another embodiment, the material can also comprise polypropylene fibers. In still another embodiment, the material comprises a natural skin.

In another aspect, provided herein is a method of treating material that is contaminated with SARS-CoV-2 or a variant thereof, comprising exposing the material to vapor, wherein the vapor is produced by heating and/or vaporizing a dry cleaning solvent, and wherein the method at least partially deactivates the virus.

In yet another aspect, provided herein is a method of treating material that is contaminated with SARS-CoV-2 or a variant thereof, comprising exposing the material to heat and dry cleaning solvent, and wherein the method at least partially deactivates the virus.

In another embodiment, the vapor is produced in a rotating drum, where said drum tumbles the material such that the material is contacted by the vapor. In an embodiment, the material is a material that has been identified as being contaminated with SARS-CoV-2 or is potentially contaminated with SARS-CoV-2. In yet another embodiment, the vapor is injected into the rotating drum at a pressure of 0.5 psi-1000 psi.

DETAILED DESCRIPTION

Provided herein is a method of treating material that is contaminated with a virus. The material can be a fabric, such as an article of clothing or household fabric, such as a blanket, towel, or tablecloth. The material can also be clothes, linens, sheets, blankets, rugs, carpets, draperies, coats, and mixtures thereof. In other embodiments, the material is any item made of fabric. In other embodiments, the material is any item made of natural skins.

In an embodiment, the material is a material that has been identified as being contaminated with SARS-CoV-2 or is potentially contaminated with SARS-CoV-2.

In embodiments, the method relies on a vapor that is introduced to the material in order to deactivate the virus. As necessary, the vapor is produced at a particular temperature and/or pressure. The vapor can be exposed to the material as part of a dry cleaning process. The source of the vapor can be a solvent, such as a dry cleaning solvent, such as D5. The vapor can be produced during one or more cycles of the dry cleaning process, such as the washing cycle or drying cycle of the dry cleaning process. The source of the vapor can also be water, producing steam vapor, either alone or in combination with a dry cleaning solvent.

Thus, in an aspect, provided herein is a method of treating material that is contaminated with a virus, comprising exposing the material to vapor, heat, and dry cleaning solvent. In an embodiment, the virus is SARS-CoV-2 or a variant thereof. The vapor can be produced by heating and/or vaporizing a dry cleaning solvent. The vapor, heat, and dry cleaning solvent can be exposed to the material as part of a dry cleaning process. In an embodiment, the dry cleaning solvent is D5. The source of the vapor can be a solvent, such as a dry cleaning solvent, such as D5. The vapor can be produced during one or more cycles of the dry cleaning process, such as the washing cycle or drying cycle of the dry cleaning process. The source of the vapor can also be water, producing steam vapor, either alone or in combination with a dry cleaning solvent.

Thus, in an aspect, provided herein is a method of treating material that is contaminated with a virus, comprising exposing the material to heat and dry cleaning solvent. In an embodiment, the virus is SARS-CoV-2 or a variant thereof. The heat and dry cleaning solvent can be exposed to the material as part of a dry cleaning process. In an embodiment, the dry cleaning solvent is D5. The material can be exposed to heat during one or more cycles of the dry cleaning process, such as the washing cycle or drying cycle of the dry cleaning process.

The material can be a fabric, such as an article of clothing or household fabric item, such as a clothes, linens, sheets, blankets, rugs, carpets, draperies, coats, and mixtures thereof. The material can also comprise polypropylene fibers, which can be found in personal protective equipment, such as an n95 masks. The material can also comprise wool, polyester and/or polyester blend fibers.

The material can be cotton, hemp, wool, rayon, polyester, acrylic, silk, or nylon, or blends thereof.

In other embodiments, the material is any item made of fabric comprised of wool. In other embodiments, the material is any item made of fabric comprised of polyester. In other embodiments, the material is any item made of fabric comprised of polyester and wool. In other embodiments, the material is any item made of fabric comprised of a polyester blend. In still another embodiment, the fabric is comprised of a combination of wool, polyester and/or a polyester blend.

As used herein, "COVID-19" refers to a contagious disease caused by the coronavirus SARS-CoV-2 and emerging variants thereof. COVID-19, also known as Covid-19, is the viral illness responsible for the global pandemic which originated in Wuhan, China, in December 2019. It is characterized by a wide variety of symptoms, ranging from none to life-threatening illness. Severe cases typically involve respiratory compromise and/or cardiovascular collapse, potentially leading to multisystem organ failure and/or death.

As used herein, "deactivate a virus" means reduce the ability of the virus to infect a host cell and/or reproduce within a host cell. In some embodiments, "deactivate a virus" means reduce the ability of the virus to cause disease in a subject. In some embodiments, "deactivate a virus" means reduce the ability of the virus to cause severe disease in a subject, where severe disease is characterized by respiratory insufficiency or failure and/or cardiovascular insufficiency or failure. For example, without limitation, destruction or disruption of the lipid-containing coating or envelope of a virus results in deactivation of the virus. SARS-COV-2 is an enveloped virus that is surrounded by a lipid bilayer.

The virus, such as SARS-CoV-2 or a variant thereof, can be deactivated by at least 5, 10, 15, 20, 25, 30, 35, 40, 45, 50, 55 60, 65, 70, 75, 80, 85, 90, 95, or 100 percent.

As used herein, "host cell" refers to any cell capable of being infected by the virus. In certain embodiments, a host cell is a naturally occurring mammalian cell. In certain embodiments, a host cell is part of a cell line. In certain embodiments, a host cell is a mammalian cell that has been modified so that it is capable of being infected by the virus. In certain embodiments, a host cell is a cell of a subject.

As used herein, a "subject" is a mammal. In certain embodiments, a subject is selected from the group consisting of mice, rats, bats, guinea pigs, rabbits, cats, dogs, sheep, goats, pigs, horses, cows, non-human primates, and humans. In certain embodiments, a subject is a human.

In an embodiment, the virus, such as a coronavirus, is deactivated during a standard dry cleaning process, using solvent with or without water, wherein the vapor that comprises solvent and/or water is introduced into the system at the temperature and/or pressure that is described herein. In another embodiment, the virus, such as a coronavirus, is deactivated with vapor produced from a dry cleaning solvent, such as D5, during either the washing cycle or the drying cycle. In embodiments, the dry cleaning solvent vapor does not comprise steam from water. In another embodiment, the dry cleaning solvent vapor comprises D5 and steam from water. In still another embodiment, the vapor is steam from water, wherein the vapor does not comprise any dry cleaning solvent. In another embodiment, the virus, such as a coronavirus, is deactivated with dry cleaning solvent, such as D5, during either the washing cycle or the drying cycle. In another embodiment, the virus, such as a coronavirus, is deactivated with heat and dry cleaning solvent, such as D5, during either the washing cycle or the drying cycle.

Thus, provided herein is a method of treating material that is contaminated with a virus, comprising exposing the material to vapor, wherein the vapor is produced by heating and/or vaporizing a dry cleaning solvent, and wherein the method at least partially deactivates the virus. The material can be a fabric, such as an article of clothing or household fabric item, such as a clothes, linens, sheets, blankets, rugs, carpets, draperies, coats, and mixtures thereof. The material can also comprise polypropylene fibers, which can be found in personal protective equipment, such as an n95 masks. The material can also comprise wool, polyester and/or polyester blend fibers.

In an embodiment, the material is a material that has been identified as being contaminated with SARS-CoV-2 or is potentially contaminated with SARS-CoV-2.

In an embodiment, the virus, such as a coronavirus, is deactivated during a standard dry cleaning process, using heat and dry cleaning solvent, wherein the material is exposed to the dry cleaning solvent at the temperature and/or pressure that is described herein. In another embodiment, the virus, such as a coronavirus, is deactivated with dry cleaning solvent, such as D5, during either the washing cycle or the drying cycle. In another embodiment, the dry cleaning solvent comprises D5 and water.

Thus, provided herein is a method of treating material that is contaminated with a virus, comprising exposing the material to heat and dry cleaning solvent, wherein the method at least partially deactivates the virus. The material can be a fabric, such as an article of clothing or household fabric item, such as a clothes, linens, sheets, blankets, rugs, carpets, draperies, coats, and mixtures thereof. The material can also comprise polypropylene fibers, which can be found in personal protective equipment, such as an n95 masks. The material can also comprise cotton, hemp, wool, rayon, polyester, acrylic, silk, or nylon, or blends thereof.

In an embodiment, the virus, such as a coronavirus, is deactivated during a standard dry cleaning process, using vapor, heat and dry cleaning solvent, wherein the material is exposed to the dry cleaning solvent at the temperature and/or pressure that is described herein. In another embodiment, vapor is introduced into the system at the temperature and/or pressure that is described herein. In another embodiment, the virus, such as a coronavirus, is deactivated with dry cleaning solvent, such as D5, during either the washing cycle or the drying cycle. In another embodiment, the dry cleaning solvent comprises D5 and water. In another embodiment, the virus, such as a coronavirus, is deactivated with vapor produced from a dry cleaning solvent, such as D5, during either the washing cycle or the drying cycle. In embodiments, the dry cleaning solvent vapor does not comprise steam from water. In another embodiment, the dry cleaning solvent vapor comprises D5 and steam from water. In still another embodiment, the vapor is steam from water, wherein the vapor does not comprise any dry cleaning solvent.

Thus, provided herein is a method of treating material that is contaminated with a virus, comprising exposing the material to vapor, heat and dry cleaning solvent, wherein the method at least partially deactivates the virus. The material can be a fabric, such as an article of clothing or household fabric item, such as a clothes, linens, sheets, blankets, rugs, carpets, draperies, coats, and mixtures thereof. The material can also comprise polypropylene fibers, which can be found in personal protective equipment, such as an n95 masks. The material can also comprise cotton, hemp, wool, rayon, polyester, acrylic, silk, or nylon, or blends thereof.

The method provided herein can be used to treat any number of viruses. Viruses that can be treated by the methods disclosed herein include, for example adenovirus, coxsackievirus, echovirus, enterovirus, hepatitis, and poliovirus. In an embodiment, the virus is coronavirus. In another embodiment, the virus has a lipid-containing coating, and the method destroys or disrupts the lipid-containing coating.

In non-limiting embodiments, a fabric, such as an article of clothing or household fabric, is placed in the washing or extraction chamber (referred to as the "basket" or "drum"), which constitutes the core of the machine. The washing chamber contains a perforated drum that rotates within an outer shell. The shell holds the solvent while the rotating drum holds the garment load.

In an aspect, provided herein is a method of treating material that is contaminated with SARS-CoV-2 virus or a variant thereof, comprising exposing the material to vapor, heat, and D5, wherein the vapor is produced by heating and/or vaporizing D5, and wherein the method at least partially deactivates the virus.

Dry Cleaning Process

In an embodiment, the dry cleaning process contains the elements of a normal dry cleaning process with additional steps that deactivate the virus. In an embodiment, the virus is SARS-CoV-2 or a variant thereof. The dry cleaning process is performed over the course of two cycles; the wash cycle and the drying cycle. The deactivation of the virus can be performed in the wash cycle, the dry cycle, or in both cycles. Each cycle is performed by combining a number of steps. Each step can be customized to create a desired result. The dry cleaning machine can run various processes depending on the type of clothing or fabric which is to be cleaned.

The first cycle is the wash cycle. During the wash cycle, the chamber is partially filled with solvent, wetting out the clothing, and the chamber begins to rotate. The rotation agitates the clothing or other fabrics to be cleaned. In an embodiment, the solvent temperature can be an ambient temperature. In another embodiment, the solvent temperature can be controlled by raising or lowering the temperature as required. During the wash step, the solvent in the chamber is circulated out of the chamber and then back into the chamber, saturating the clothing or other fabrics. In another embodiment, the solvent is passed through a filter before returning to the chamber. In another embodiment, the solvent filter is bypassed for a given period of time before the filter is used. This process is known as the wash step and is continued for the wash duration. In another embodiment, the solvent is then removed and is sent to a distillation unit consisting of a distillation chamber and condenser. The condensed solvent is fed into a separator unit where water in the solvent is separated from the solvent. The remaining solvent is then fed into the "clean solvent" tank. In another embodiment, the solvent is then removed and returned to a holding tank.

A typical wash step lasts for the number of minutes described herein. A dry cleaning surfactant soap or other cleaning aid can also be added in addition to the dry cleaning solvent.

In an embodiment, the deactivation of the virus is incorporated into the wash cycle. The deactivation of the virus consists of vapor introduced into the chamber while the clothing tumbles. The vapor is composed of silicone fluid. The vapor can be created externally and introduced to the chamber. The vapor can also be created by the fluid already in the chamber.

In an embodiment, the clothing is saturated with silicone fluid and then heated. The fluid vaporizes and the clothing is tumbled in its presence. This is called the vapor step. The vapor step lasts for a predetermined amount of time. The vapor step can be before the wash step, during the wash step, or after the wash step. In another embodiment, the vapor step replaces the wash step.

At the end of the wash step, the machine can start a rinse step where the fabric is rinsed with freshly distilled or filtered solvent dispensed from one of the solvent tanks. This process is known as the "second bath" or the "rinse step." In an embodiment, the vapor step occurs during the rinse step. In another embodiment, the vapor step occurs after the rinse step.

After the rinse step, the machine begins the extraction step, which extracts, via centrifugal force, a portion of the solvent remaining in the clothing or other fabrics. Modern machines can recover most of the solvent employed. The extraction step begins by draining the solvent from the washing chamber and accelerating the basket from 40 to 1000 rpm, causing much of the solvent to spin free of the fabric. In an embodiment, the extraction is done at a single speed. In another embodiment, the extraction is done at multiple speeds over a series of steps. After extraction, the machine starts the drying cycle.

The drying cycle consists of two steps. The first step is the drying step. During the drying step, the garments are tumbled in a stream of warm air that circulates through the basket. The temperature of the air is controlled to a desired temperature. The remaining solvent within the clothing or textiles evaporates in the warm air. The warm air exhaust is then drawn over a chilled evaporator, which is colder than the air stream, and the solvent condenses. The condensed solvent is then fed into a separator unit where the water in the solvent is separated from the solvent. The remaining solvent is then fed into a holding tank for reuse. Modern dry cleaning machines employ a closed loop system in which the chilled air is reheated and recirculated. This results in high solvent recovery rates and reduced air emissions.

After the drying step is complete, a cool-down step begins. In this step, the heat is turned off, the air is allowed to continue passing through the basket, and then over the chiller evaporator. The cool air then returns into the basket and further cools the basket and the garments within the basket. This has the effect of reducing the air temperature inside the basket until a desired temperature is reached. A cooler temperature will reduce wrinkling and allow workers to handle the finished garments safely.

In an embodiment, the vapor step is incorporated into the dry cycle. The vapor step can occur before the drying step, during the drying step, or after the drying step. The vapor step also can occur before the cool-down step, during the cool-down step, or after the cool-down step. In an embodiment, the clothing is gently extracted after the wash cycle. The light extract can be performed by utilizing a slow extraction speed or a high extraction speed for a short time. The drying step begins and the clothing is heated. When the clothing has reached a sufficient temperature, the movement of air within the basket is temporarily stopped, allowing the vapor to remain in contact with the clothing longer. The clothing is tumbled in the vapor to encourage high contact with the vapor. After a sufficient time, the dry step returns to full air circulation. In one embodiment, the clothing is extracted once more prior to resuming the drying step. There can be multiple vapor steps within the drying cycle.

After the cool-down step, the drying cycle is now complete and thus the dry cleaning process is complete. After the dry cleaning process, the garments are clean and ready for pressing and finishing.

While the deactivation of the virus is normally incorporated into a standard dry cleaning process, in an embodiment, the deactivation of the virus can be performed in the absence of a dry cleaning process. For example, the clothing can be passed through a vapor and then dried in a continuous process. In one embodiment, the material that is contaminated with a virus is treated by a system and method for dry cleaning articles using a dry cleaning solvent.

In an embodiment, the material and dry cleaning solvent are added to the chamber. The material is washed for a given period of time with or without filtration or in a stepwise combination. In an embodiment, a portion of the dry cleaning solvent is extracted by accelerating the chamber at a given rate and for a given amount of time. In an embodiment, the chamber accelerates at a slower given rate and is heated until a given temperature is reached. In an embodiment, the heating stops, and the vapor forms around and through the material. In a further embodiment, this step lasts for a given period of time, after which the chamber accelerates to a given rate, removing the remaining solvent from the material.

Thus, provided herein is a method of treating material that is contaminated with SARS-CoV-2, comprising exposing the material to vapor, heat, and dry cleaning solvent. In an embodiment, the material is exposed to a dry cleaning solvent, such as D5. This step can be referred to as a "washing cycle," and can also occur in a chamber of a dry cleaning machine. The exposure can take place for any of the time durations described herein. Then, a portion of the dry cleaning solvent can optionally be removed by, for example, extraction. The material and dry cleaning solvent are then heated to any of the temperatures described herein, and a dry cleaning solvent vapor forms around and through the material. This step can be referred to as a "drying cycle." This step can also occur in a chamber of a dry cleaning machine. The material is exposed to the vapor for any of the time durations described herein. The solvent and vapor can then be removed. This process deactivates SARS-CoV-2. In an embodiment of this method, the chamber of the dry cleaning machine is at a temperature of 0° C. to 85° C. In another embodiment of the method, the chamber of the dry cleaning machine is heated to a temperature of 70° C. to 85° C. In still another embodiment of the method, the chamber of the dry cleaning machine is heated to a temperature of 70° C. to 85° C. In still another embodiment of the method, the chamber of the dry cleaning machine is heated to a temperature of 70° C. These temperatures can occur during the washing cycle, the drying cycle, or both.

The dry cleaning process can take place in any number of dry cleaning machines. Such machines are described in U.S. Pat. Nos. 8,613,804 and 8,123,819, both of which are incorporated herein by reference in their entireties.

Dry cleaning solvents useful herein include any hydrocarbons and hydrocarbons blended with other chemicals. In addition, the solvent used in the methods of the present invention can comprise an organo-silicone, i.e., an organic/inorganic hybrid solvent. Organo-silicones useful herein include cyclic siloxanes and linear siloxanes. The chemical characteristics of these cyclic and linear siloxanes allow the dry cleaning systems according to an exemplary embodiment of the present invention to operate without dependency on distillation.

Any suitable cyclic or linear siloxane can be used with the present invention, such as those described in U.S. Pat. No. 6,042,618, the entire contents of which are incorporated herein by reference. Of these siloxanes, decamethylcyclopentasiloxane, a pentamer commonly referred to as D5, is presently preferred.

In an embodiment, the dry cleaning solvent is a siloxane-based solvent. In an embodiment, the siloxane-based solvent is decamethylcyclopentasiloxane (D5), octamethyltetracyclosiloxane, or dodecamethylhexacyclosiloxane. In still another embodiment, the siloxane-based solvent is decamethylcyclopentasiloxane (D5).

In an embodiment, the dry cleaning solvent has a flash point of at least 43° C., 49° C., 54° C., 60° C., 66° C., 71° C., or 77° C. In another embodiment, the flash point is 54° C.-66° C. In another embodiment, the flash point is 57° C.-63° C. In another embodiment, the flash point is at least 60° C. In another embodiment, the flash point is 77° C.

In embodiments, the material is exposed to the vapor for 3-75 minutes, 10-70 minutes, 15-65 minutes, 20-60 minutes, 25-55 minutes, 30-50 minutes, or 35-45 minutes. In other embodiments, the material is exposed to the vapor for 3, 5, 10, 15, 20, 25, 30, 35, 40, 45, 50, 55, 60, 65, 70, or 75 minutes. In the method, the vapor reaches a temperature of at least 50° C., at least 55° C., at least 60° C., at least 65° C., at least 70° C., at least 75° C., at least 80° C., at least 85° C., or at least 90° C. The vapor can reach a temperature of 50° C.-90° C., 55° C.-85° C., 60° C.-80° C., 65° C.-75° C., or 68° C.-72° C.

In embodiments, the material is exposed to the dry cleaning solvent for 3-75 minutes, 5-75 minutes, 10-70 minutes, 15-65 minutes, 20-60 minutes, 25-55 minutes, 30-50 minutes, or 35-45 minutes. In other embodiments, the material is exposed to the dry cleaning solvent for 3, 5, 10, 15, 20, 25, 30, 35, 40, 45, 50, 55, 60, 65, 70, or 75 minutes.

In the method, the drying cleaning solvent reaches a temperature of at least 50° C., at least 55° C., at least 60° C., at least 65° C., at least 70° C. The drying solvent can reach a temperature of 50° C.-90° C., 55° C.-85° C., 60° C.-80° C., 65° C.-75° C., or 68° C.-72° C. In embodiments of the methods provided herein, wherein the vapor is produced as part of a dry cleaning process. In embodiments of the method, the vapor is produced during the drying cycle of a dry cleaning process. In other embodiments, the vapor is produced during the washing cycle of a dry cleaning process.

The vapor can be produced in a rotating drum, where said drum tumbles the material such that the material is contacted by the vapor. The vapor can be introduced into the rotating drum at an appropriate pressure, such as 0.5 psi-1000 psi, such as 70 psi, 80 psi, 90 psi, 100 psi, 110 psi, 120 psi, 130 psi, 140 psi, 150 psi, 160 psi, 170 psi, 180 psi, 190 psi, 200 psi, 210 psi, or 220 psi.

In an embodiment of the method, the rotating drum or chamber of the dry cleaning machine is at a temperature of 0° C. to 85° C. In another embodiment of the method, the rotating drum or chamber of the dry cleaning machine is heated to a temperature of 70° C. to 85° C. In still another embodiment of the method, the rotating drum or chamber of the dry cleaning machine is heated to a temperature of 70° C. to 85° C. In still another embodiment of the method, the rotating drum or chamber of the dry cleaning machine is heated to a temperature of 70° C. These temperatures can occur during the washing cycle, the drying cycle, or both.

In an embodiment of the method provided herein, 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60% of the virus is deactivated.

In an embodiment, the methods provided herein reduce the amount of virus on the material. In another embodiment, 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60% of the virus is reduced.

The term "vaporizing" refers to transitioning or converting into vapor.

Experimental

I. Objective

The emergent threat of COVID-19 infection originating from SARS-CoV-2 and the high rate of transmission associated severe illness and fatalities, has created a needed response for rapid development and evaluation of effective countermeasures. Testing and evaluation was conducted on a modified dry cleaning process in simulated testing against SARS-CoV-2 contaminated fabric. The dry cleaning fluid, dry cleaning heat, wash and spin cycles, and enhanced vapor effects during the simulated washing and drying cycles in the drying process were evaluated in independent tests for measuring efficacy in the destruction of SARS-CoV-2.

II. Equipment

1. Heating cabinet equipped with heat source, recirculation fans, drying grate, and vapor exposure manifold
2. Omega digital temperature monitor with type K thermocouple
3. SKC vapor diffusion cells with temperature regulated heat block
4. Omega digital flow meter and flow controller
5. Beckman centrifuge and vortex
6. Electric tumbler III. Methods—Testing Description The tested cleaning solution is used as a silicone based environmentally friendly, non-toxic, non-hazardous and extremely gentle alternative to petrochemicals. The silicone based solution is used as a medium in the dry cleaning process. The silicone medium offers a sustainable alternative to conventional washing and reduces the amount of water required and the amount of energy needed. This testing evaluated the silicone based solution for efficacy in SARS-CoV-2 decontamination from clothing material in simulated dry cleaning trials.

The test fabric consisted of 71% wool, 25% polyester, and 4% polyester blend in a tight material weave. The silicone consisted of pure decamethylcyclopentasiloxane (100% D5). The solution (100% D5) has a high flash point (77° C.), and low surface tension (17.42 dynes/cm$^2$), which provides vaporization and penetration through fabric materials during the dry cleaning process.

Testing was conducted to evaluate the specific dry cleaning solution (100% D5), in individual dry cleaning process steps, and the overall dry cleaning process to evaluate efficacy in the destruction of SARS-CoV-2 contaminated fabric.

The log reduction effectiveness of the dry cleaning process was tested against an envelope virus (SARS-CoV-2) strain USA-WA1/2020. The complete genome of USA-WA1/2020 has been sequenced. The Isolate GenBank: MN985325 and after one passage in Vero cells GenBank: MT020880. The complete genome of SARS-CoV 2 strain USA-WA1/2020 has been sequenced after four passages in collaboration with Database for Reference Grade Microbial Sequence (FDA-ARGOS; GenBank: MT246667). Each vial used on study contained approximately 0.5 mL of cell lysate and supernatant from *Cercopithecus aethiops* kidney cells infected with SARS-CoV-2 isolate USA-WA1/2020.

The dry cleaning process as modified and utilized in a temperature and humidity controlled biological level 3 laboratory environment. Testing evaluated SARS-CoV-2 inoculated wool blend fabric coupons with the addition of 100% D5 solution wash medium, fabric coupons without wash additive, dry cleaning heat, and silicone medium vapor production during the drying process in the deactivation of viable virus.

Additional testing was conducted to evaluate the wash and rinse removal/deactivation of the virus from wool coupons. For test result evaluation, positive control coupons were similarly prepared to test coupons and kept at standard room environmental conditions over the same time course as tested coupons, without being subjected to any of the dry cleaning processes. The positive control coupons served as viral concentration standards to define the efficacy of the various dry cleaning process conditions in deactivating the SARS-CoV-2 virus from test coupons. A test matrix showing the associated tests, testing dates in headers, coupon test processing, exposure conditions, and samples is shown in Table 1.

TABLE 1

| | Dry Cleaning Process Testing against SARS-CoV-2 | | | | | |
|---|---|---|---|---|---|---|
| Test Conditions | Fabric pre-virus application silicone solution wet and wrung (Yes/No) | SARS-CoV-2 fabric coupon Inoculation volume (μl) | Fabric coupon size (sq. in.) | Number of test coupons | Coupon exposure test cabinet temperature (° C.) | Test Chamber fabric coupon exposure test time (min) |
| Test evaluation of silicone additive and dry cleaning process phase efficacy. Test conducted Jun. 25, 2020 | | | | | | |
| Virus only Room temperature positive control | No | 200 | 4 | 3 | 23 | 45 |
| Virus and silicone liquid room temperature positive control | Yes | | | 3 | 23 | 45 |
| Heat only exposure | No | 200 | 4 | 3 | 70 | 15 |
| | | | | 3 | | 30 |
| | | | | 3 | | 45 |
| Heat and silicone liquid | Yes | | | 3 | 70 | 15 |
| | | | | 3 | | 30 |
| | | | | 3 | | 45 |
| Heat and silicone liquid + vapor | Yes | | | 3 | 70 | 15 |
| | | | | 3 | | 30 |
| | | | | 3 | | 45 |
| Green Earth Wash and Spin Rinse cleaning process testing. Test conducted Sep. 4, 2020 | | | | | | |
| *Virus only positive control | No | 200 | 4 | 3 | 23 | 45 |
| *Complete cycle wash and rinse | Fabric rotary tumble wash in 3 ounces of silicone solution | | | 3 | NA | 45 |

TABLE 1-continued

Dry Cleaning Process Testing against SARS-CoV-2

| Test Conditions | Coupons subjected to simulated wash & spin cycles (yes/No) | Coupon fabric silicone solution wash volume (mL) | Silicone solution rotary wash cycle (RPM) | Silicone solution rotary wash cycle time (min) | Centrifuge post-wash wringing cycle (RPM) | Centrifuge post-wash wringing cycle time (min) |
|---|---|---|---|---|---|---|
| Test evaluation of silicone additive and dry cleaning process phase efficacy. Test conducted Jun. 25, 2020 | | | | | | |
| Virus only Room temperature positive control | No | NA | NA | NA | NA | NA |
| Virus and silicone liquid room temperature positive control | No | NA | NA | NA | NA | NA |
| Heat only exposure | No | NA | NA | NA | NA | NA |
| Heat and silicone liquid | No | NA | NA | NA | NA | NA |
| Heat and silicone liquid + vapor | No | NA | NA | NA | NA | NA |
| Green Earth Wash and Spin Rinse cleaning process testing. Test conducted Sep. 4, 2020 | | | | | | |
| *Virus only positive control | No | NA | NA | NA | NA | NA |
| *Complete cycle wash and rinse | Yes | 89 mL | 35 | 16 | 500 | 4 |

*Additional tests conducted to evaluate the wash - spin rise cycle of the cleaning process. Rotary tumbler wash process.

Figure 1:
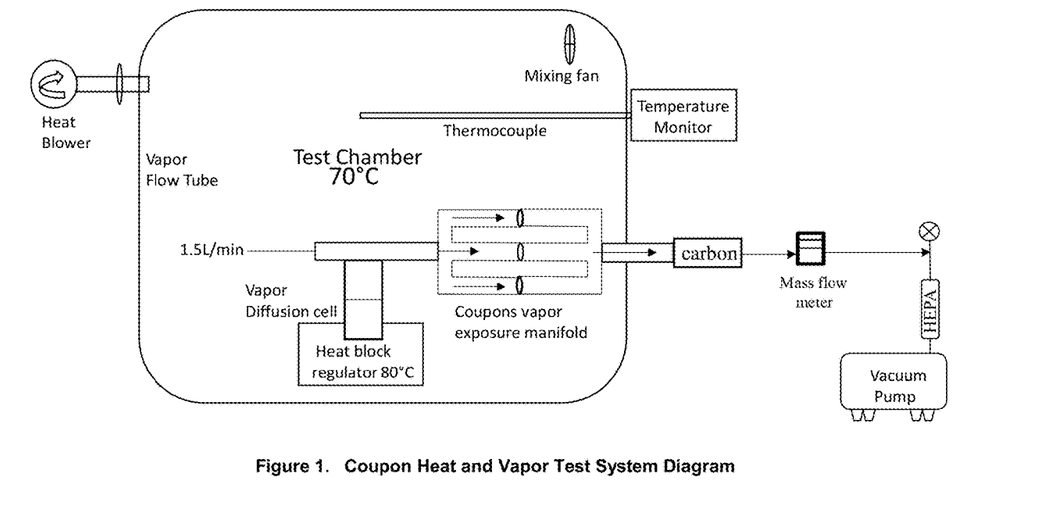
FIG. 1 shows a diagram of the test system.

Preceding the initiation of the study, wool blend fabric material test samples were autoclaved steam sterilized to eliminate potential biological contamination of the test fabric or contamination interference in sample analysis. Tests were conducted over three time variables of either 15, 30, or 45 minutes. Test and positive viral control coupons for all testing were prepared in a class 2 biological safety cabinet using a common viral stock with known titer (range $1 \times 10^6$ to $1 \times 10^7$ pfu/mL). Individual fabric test coupons, either pre-dampened with solution additive, dry, or wash/rinse processed (test dependent), were placed in coupon and test identification labeled sterile petri dishes. Coupons were inoculated from a standard stock viral suspension with 200 mL of SARS-CoV-2 virus using a calibrated micropipette. The viral suspension was then evenly coated over the test coupons using sterile cell spreaders. Coated test coupons and positive control coupons were air dried over the same time course at standard laboratory conditions (30-50 min) in the biological level 2 safety cabinet prior to testing. Testing was performed to evaluate the following (1) heat, (2) heat and silicone liquid, and (3) heat, silicone liquid, and vapor production during dry cleaning cycles were characterized in independent test trials. Tests were conducted using an environmental chamber equipped to simulate each of the three (3) dry cleaning processes in the deactivation of SARS-CoV-2. The chamber was housed in a sterile biological level 2 safety cabinet, and was equipped with internal heaters, temperature regulators, monitors, and controllers. The test chamber internal temperature was maintained at 70° C. for all coupon exposure tests simulating heat levels in the drying phase of the cleaning process. A fan was used at low flow to provide heat recirculation and temperature homogeneity in the test chamber and was measured using a type K thermocouple probe located in the center of the chamber equipped with a calibrated digital temperature monitor. For the vapor test phase of the study, a heat block temperature regulated diffusion cell was housed in the test chamber and regulated at 80° C. for (D5) solution vapor diffusion into a 70° C. flow stream. The diffusion cell was filled with 10 mL of (D5) solution preceding each fabric coupon vapor exposure test. The diffusion cell was attached to a tri-branch test manifold designed to house three (3) test coupons simultaneously in one of three coupon holding tubes for simulating (D5) fabric wash solution vapor produced during the drying cycle of the dry cleaning process. The flow manifold was constructed from 1.5 inch inside diameter tubing for vapor transport across the test coupons. Air flow (70° C.) was directed from the test chamber across the diffusion cell to provide a vapor challenge to each of the three coupon holding locations. A total flow rate of 1.5 L/min was maintained to provide a low flow (500 cc/min) delivery of dilute silicone vapor across each of the three test coupons simultaneously. The approximate vaporization rate of (D5) solution from the diffusion cell was 3.6 mL over a 45 minute test period. This vapor diffusion rate equates to 80 µL/min and a volumetric generation rate of 56 µL/L of air. Vapor manifold delivery flow was provided with a Gast rotary vane vacuum pump with valve control, and a digital flow meter to monitor the flow rate during testing. Non-silicone vapor exposed test coupons (subjected only to heat) were placed on a perforated steel rack in the environmental test chamber. A diagram of the test system is shown in FIG. 1.

Additional testing was conducted to evaluate the wash and rinse process. The additional testing was conducted on evaluated wash and rinse cycle removal/deactivation of SARS-CoV-2 from the same clothing type (wool blend) used in all tests. For these tests, a rotary tumbler was used to agitate individual SARS-CoV-2 inoculated test fabric coupons in 8 oz. displacement mason jars. The jars were filled with 3 oz., or 89 mL of (100% D5) solution to simulate the wash solution volume displacement of an actual wash unit used in the dry cleaning process. These test fabric coupons were pinned to wire frames that negated the fabric from sticking to the jar wall and allowed for actual fabric agitation and flushing action to closely simulate the actual washing process. These test coupons (3) were rotary tumbled in individual jars at approximately 35 RPM for 16 minutes. Following the wash cycle simulation, the coupons were sterile transferred into individually labeled 50 mL filter separation conical tubes and spin cycled at 500 rpm for 4 minutes in a lab centrifuge. These tests were conducted for evaluation of the washing cycle portion of the individual dry cleaning process, and total combined processes in the deactivation/destruction of SARS-CoV-2 contaminated fabric.

IV. Methods—Preparing Virus Coupons

Square wool blend fabric coupons with dimensions of 2 inch×2 inch were inoculated from a viral stock (range $1\times10^6$ to $1\times10^7$ pfu/mL) with 200 µl of neat virus inoculum using a calibrated pipette. The virus inoculum was then spread uniformly on the center area ~1.5 inch×1.5 inch of each test coupon. Three (3) coupons were designated as positive control concentration baseline coupons. Viral baseline and test process coupons were air dried in a class 2 biological safety cabinet (BL2) for approximately 30 to 50 minutes. The three (3) positive control viral concentration baseline coupons were kept at room temperature inside of the BL2 cabinet during dry cleaning process testing. Positive control baseline concentration coupons were extracted and plated for viral titer following dry cleaning process testing at the same time points as test process coupons. Test and positive control baseline coupons were placed in individually labeled 50 mL conical tubes containing 2 mL of DMEM media. Samples were then vortexed for 1 minute at 50% speed for viral extraction and assayed for viral enumeration and the calculation of viral deactivation efficiency.

V. Sample Analysis and Results Stock virus used for test and control coupon inoculation (SARS-CoV-2, strain USA-WA1/2020) were concentration titered by serial dilution to obtain the 50% tissue culture infectious dose ($TCID_{50}$). This was conducted to ensure that sufficient quantities of virus were available for testing. Untreated virus control concentrations were assessed to ensure that titers remained consistent. For cell and virus cultures, sterile DMEM (Mediatech) supplemented with 7% fetal bovine serum (HyClone), GlutaMax (Gibco), and penicillin-streptomycin-neomycin antibiotic mixture (Gibco) were utilized. Vero E6 cells (monkey kidney cells) that were originally obtained from ATCC (CRL-1586) were used for assays with ASFV. All cells were maintained at 36°-38° C. and 5% $CO_2$ in a humidified atmosphere, and cells were seeded into flasks for propagation and expanded into 96-well plates for titration of SARS-CoV-2 virus. Cells were infected with viral coupon sample extractions at 70% confluence and observed for the presence of cytopathic effect (CPE) for four (4) to five (5) days post-infection. A 10× serial dilution of coupon sample viral extractions was applied to cell assay plates at up to an 8-log dilution factor for the presence of viral growth into the plate host cells. Plates were inoculated with 5 replicate samples at each dilution level, with each row of replicates 10× more dilute than that used in the preceding row for viral cell infectivity detection. Viral propagation plate readings were conducted under high intensity magnification of each plate cell for viral host cell infectivity and recorded on a sample test log for positive (+) or negative (−) viral propagation. Data was entered into a Reed & Muench calculation for sample concentration measurement and determination of the $TCID_{50}$ (50% tissue culture infectious dose of a virus).

VI. Test Results

Coupon preparation including SARS-CoV-2 inoculation, drying, exposure testing, extractions, and cell assay plating was conducted in a sterile class 2 biological safety cabinet. Following a 4 day plate assay viral incubation period, plates were read for viral infectivity and data recorded on $TCID_{50}$ test logs. Results were entered into a Reed Muench data analysis program for results and comparison of positive test control sample viral titer concentrations to dry cleaning process exposed test coupon results. Tabulated data from the $TCID_{50}$ test results with individual drying cycle simulation, individual washing cycle simulation, and the complete dry cleaning process measures the efficacy in deactivating SARS-CoV-2. The averaged viral $TCID_{50}$ deactivation of the test coupons tested at each dry cleaning process condition are shown in Table 2. The individual test sample $TCID_{50}$ results are tabulated in Table 3.

TABLE 2

Individual Dry Cleaning Process and Total Dry Cleaning Process Test Results

GreenEarth Modified Drying Cycle Simulation Test Results Jun. 25, 2020

| Condition | Number of Replicates | Time (minutes) | Average of Test Replicates TCID50 | Average of Test Replicates Log10 TCID50 | Log10 Reduction to virus control | Percent Log Reduction to Virus Control | Averaged Test Sample Percent Log Reduction to Averaged Virus Controls |
|---|---|---|---|---|---|---|---|
| Virus Control at room temperature | 3 | 45 | 4755.95 | 3.68 | NA | NA | NA |
| Silicone Liquid Control | 3 | 45 | 31.62 | 1.50 | NA | NA | |
| Heat Only | 3 | 15 | 5336.24 | 3.73 | −0.05 | −12.20% | 14.28% |
| | 3 | 30 | 4755.95 | 3.68 | 0.00 | 0.00% | |
| | 3 | 45 | 2138.82 | 3.33 | 0.35 | 55.03% | |
| Heat + Silicone Vapor | 3 | 15 | 3389.80 | 3.53 | 0.15 | 28.72% | 37.74% |
| | 3 | 30 | 2509.91 | 3.40 | 0.28 | 47.23% | |
| | 3 | 45 | 2983.03 | 3.47 | 0.20 | 37.28% | |
| Heat + Silicone Liquid | 3 | 15 | 789.83 | 2.90 | 0.78 | 83.39% | 75.43% |
| | 3 | 30 | 1125.46 | 3.05 | 0.63 | 76.34% | |
| | 3 | 45 | 1590.08 | 3.20 | 0.48 | 66.57% | |
| Heat + Liquid + Vapor | 3 | 15 | 94.92 | 1.98 | 1.70 | 98.00% | 96.74% |
| | 3 | 30 | 138.31 | 2.14 | 1.54 | 97.09% | |
| | 3 | 45 | 232.01 | 2.37 | 1.31 | 95.12% | |

TABLE 2-continued

Individual Dry Cleaning Process and Total Dry Cleaning Process Test Results

| Condition | Number of Replicates | Time (minutes) | Average of Test Replicates TCID50 | Average of Test Replicates Log10 TCID50 | Log10 Reduction to virus control | Percent Log Reduction to Virus Control | Averaged Test Sample Percent Log Reduction of complete dry cleaning process |
|---|---|---|---|---|---|---|---|
| GreenEarth Wash, Spin Rinse Washing Cycle Simulation Test Results Sep. 4, 2020 | | | | | | | |
| Virus Control at Room Temperature | 3 | 45 | 88342.62 | 4.90 | NA | NA | NA |
| Silicone wash, and spin cycle | 3 | 45 | 35138.40 | 4.54 | 0.36 | 56.18% | 56.18% |
| GreenEarth Drying Cycle and Washing Cycle Combined Test Results | | | | | | | |
| Complete cycle - silicone wash, spin, heat and vapor | 3 | 45 | 35138.40 | 4.54 | 0.36 | 56.18% | 98.57% |

TABLE 3

$TCID_{50}$ Individual Sample ID and Results

| Test Condition | Test Time (min) | Test Replicate | Sample ID | $TCID_{50}$ | Avg $TCID_{50}$ |
|---|---|---|---|---|---|
| Virus Control at Room Temperature | 45 | 1 | G1-1 | 7943.2823 | 4755.94589 |
| | 45 | 2 | G1-2 | 3162.2777 | |
| | 45 | 3 | G1-3 | 3162.2777 | |
| D5 Liquid Only Control | 45 | 1 | S-1 | 31.622777 | NA |
| | 45 | 2 | S-2 | 31.622777 | |
| | 45 | 3 | S-3 | 31.622777 | |
| Heat Only | 15 | 1 | G2-15-1 | 4903.1614 | 5336.24047 |
| | 15 | 2 | G2-15-2 | 7943.2823 | |
| | 15 | 3 | G2-15-3 | 3162.2777 | |
| | 30 | 1 | G2-30-1 | 7943.2823 | 4755.94589 |
| | 30 | 2 | G2-30-2 | 3162.2777 | |
| | 30 | 3 | G2-30-3 | 3162.2777 | |
| | 45 | 1 | G2-45-1 | 1995.2623 | 2138.8218 |
| | 45 | 2 | G2-45-2 | 1258.9254 | |
| | 45 | 3 | G2-45-3 | 3162.2777 | |
| Heat & D5 Vapor | 15 | 1 | G4-15-1 | 1995.2623 | 3389.8041 |
| | 15 | 2 | G4-15-2 | 5011.8723 | |
| | 15 | 3 | G4-15-3 | 3162.2777 | |
| | 30 | 1 | G4-30-1 | 5011.8723 | 2509.90772 |
| | 30 | 2 | G4-30-2 | 1258.9254 | |
| | 30 | 3 | G4-30-3 | 1258.9254 | |
| | 45 | 1 | G4-45-1 | 3162.2777 | 2983.02655 |
| | 45 | 2 | G4-45-2 | 3690.622 | |
| | 45 | 3 | G4-45-3 | 2096.18 | |
| Heat & D5 Liquid | 15 | 1 | G3-15-1 | 316.22777 | 789.827138 |
| | 15 | 2 | G3-15-2 | 794.32823 | |
| | 15 | 3 | G3-15-3 | 1258.9254 | |
| | 30 | 1 | G3-30-1 | 879.9254 | 1125.45736 |
| | 30 | 2 | G3-30-2 | 501.18723 | |
| | 30 | 3 | G3-30-3 | 1995.2623 | |
| | 45 | 1 | G3-45-1 | 1258.9254 | 1590.07555 |
| | 45 | 2 | G3-45-2 | 1415.1212 | |
| | 45 | 3 | G3-45-3 | 2096.18 | |
| | 15 | 1 | G5-15-1 | 79.432823 | 91.9193696 |
| | 15 | 2 | G5-15-2 | 79.432823 | |
| | 15 | 3 | G5-15-3 | 125.89254 | |
| | 30 | 1 | G5-30-1 | 209.618 | 138.314455 |
| | 30 | 2 | G5-30-2 | 79.432823 | |
| | 30 | 3 | G5-30-3 | 125.89254 | |
| | 45 | 1 | G5-45-1 | 125.89254 | 232.088834 |
| | 45 | 2 | G5-45-2 | 444.24142 | |
| | 45 | 3 | G5-45-3 | 125.89254 | |
| Virus Control at Room Temperature | 45 | 1 | 1-cont | 5.01E+04 | 8.83E+04 |
| | 45 | 2 | 2-cont | 6.81E+04 | |
| | 45 | 3 | 3-cont | 1.47E+05 | |

TABLE 3-continued

| | | | TCID$_{50}$ Individual Sample ID and Results | | |
|---|---|---|---|---|---|
| Test Condition | Test Time (min) | Test Replicate | Sample ID | TCID$_{50}$ | Avg TCID$_{50}$ |
| D5 Wash & Spin Cycle | 45 | 1 | 1-cont | 3.16E±04 | 3.51E±04 |
| | 45 | 2 | 2-cont | 4.22E±04 | |
| | 45 | 3 | 3-cont | 3.16E±04 | |

Figure 2:
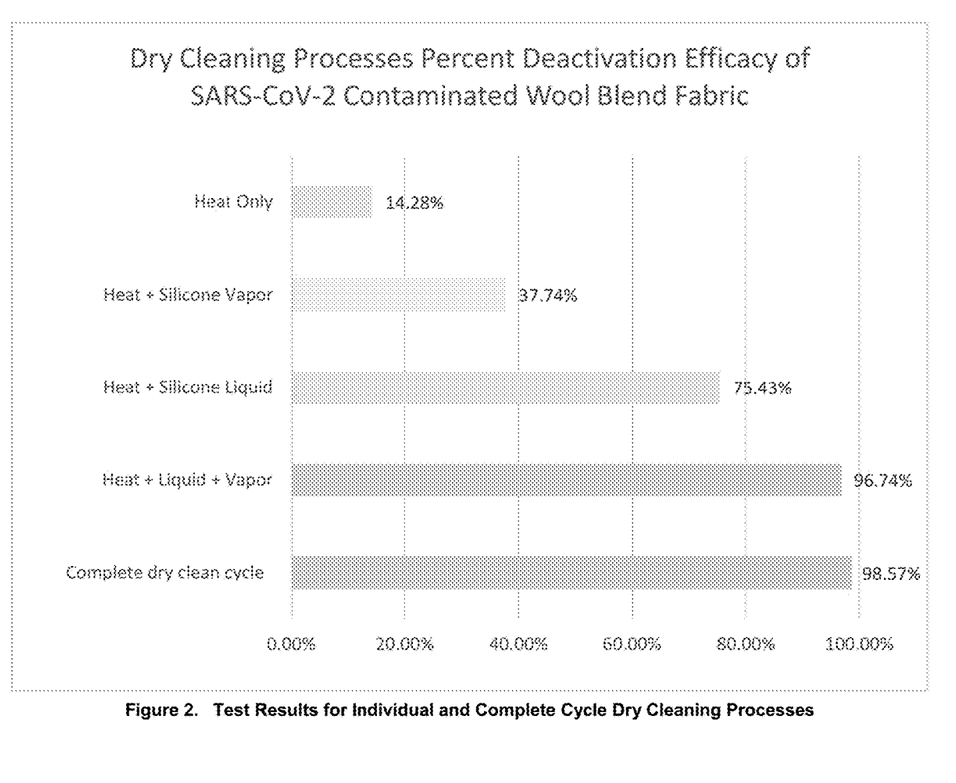
FIG. 2 shows the percent log reduction efficacy of each of the simulated dry cleaning processes and the total process in deactivating SARS-CoV-2 infected wool blend fabric material.

Data shown in Table 2 represents the individual dry cleaning process percent log reduction to the control samples for each coupon set at each process time, and averaged percent reduction of each process on viral deactivation. The silicone wash and spin rinse tests were combined with the heat, silicone liquid, and vapor exposure process results to define the overall percent viral reduction of the complete dry cleaning process. A plot showing the percent log reduction efficacy of each of the simulated dry cleaning processes and the total process in deactivating SARS-CoV-2 infected wool blend fabric material is shown in FIG. 2.

VII. Discussion

The results of the testing would suggest that (100% D5) solution dry cleaning process has a high level of efficacy in the reduction of SARS-CoV-2 contaminated clothing. This testing was conducted to provide an accurate simulation of patented dry cleaning process in a laboratory environment. Simulation of the drying cycle in a process combing heat and dry cleaning solvent (D5) provided a reduction of approximately 75.4% of viable virus. The process of combining heat, vapor and dry cleaning solvent (D5) with the drying cycle performed even better, providing a reduction of approximately 96.7% of viable virus. The combination of a washing cycle, which included dry cleaning solvent (D5), and a drying cycle, which included combining heat, vapor and dry cleaning solvent (D5), performed the best with a reduction of approximately 98.6% of viable virus.

It should be noted, that in one simulation of the drying cycle, the combination of heat, vapor, and liquid condition produced a percent log reduction to virus control of 98.00%. If this one test result were combined with average wash cycle simulation test results, the serial combination of a 56.18% wash cycle reduction and the 98.00% drying cycle reduction would produce the optimized calculated result of 99.12% log reduction to the average virus controls.

The invention claimed is:

1. A method of treating material that is contaminated with SARS-CoV-2 virus or a variant thereof, comprising exposing the material to vapor, heat, and dry cleaning solvent, wherein the vapor is produced by heating and/or vaporizing a dry cleaning solvent, and wherein the method at least partially deactivates the SARS-CoV-2 virus, wherein the method comprises the steps of
a) exposing the material to dry cleaning solvent, followed by
b) heating the dry cleaning solvent to form a vapor, wherein
the dry cleaning solvent reaches a temperature of 60° C.-80° C.,
the material and dry cleaning solvent are added to a chamber of a dry cleaning machine, wherein the dry cleaning solvent further comprises water, the vapor is produced by heating the dry cleaning solvent and water, and the vapor is produced during a drying cycle or a washing cycle, and
wherein the SARS-CoV-2 virus has a lipid-containing coating and the vapor comprises submicron liquid particles of the dry cleaning solvent that penetrate the lipid-containing coating of the SARS-CoV-2 virus.

2. The method of claim 1, wherein the material is exposed to the vapor for 3-75 minutes.

3. The method of claim 1, wherein the material is a fabric.

4. The method of claim 3, wherein the fabric is an article of clothing or household fabric item.

5. The method of claim 1, wherein the material comprises polypropylene fibers.

6. The method of claim 1, wherein the vapor reaches a temperature of at least 70° C.

7. The method of claim 1, wherein the dry cleaning solvent has a flash point of at least 60° C.

8. The method of claim 1, wherein the method destroys the lipid-containing coating.

9. The method of claim 1, wherein the dry cleaning solvent is a siloxane-based solvent.

10. The method of claim 9, wherein the siloxane-based solvent is decamethylcyclopentasiloxane (D5), octamethyltetracyclosiloxane, or dodecamethylhexacyclosiloxane.

11. The method of claim 1, wherein the vapor is produced in a rotating drum or injected into the rotating drum at a pressure of 0.5 psi-1000 psi, where said rotating drum tumbles the material such that the material is contacted by the vapor.

12. The method of claim 1, wherein the material comprises cotton, hemp, rayon, acrylic, silk, nylon, wool, polyester and/or polyester blend fibers.

* * * * *